United States Patent [19]

Frisch et al.

[11] Patent Number: 5,074,905

[45] Date of Patent: Dec. 24, 1991

[54] NOVEL SUSPOEMULSIONS OF ACTIVE INGREDIENTS FOR PLANT PROTECTION

[75] Inventors: Gerhard Frisch, Wehrheim; Konrad Albrecht, Kelkheim, both of Fed. Rep. of Germany

[73] Assignee: Hoeschst Aktiengesellschaft, Frankfurt am Main, Fed. Rep. of Germany

[21] Appl. No.: 438,978

[22] Filed: Nov. 20, 1989

Related U.S. Application Data

[63] Continuation of Ser. No. 96,909, Sep. 15, 1987, abandoned.

[30] Foreign Application Priority Data

Sep. 17, 1986 [DE] Fed. Rep. of Germany ....... 3631558

[51] Int. Cl.$^5$ ............................................. A01N 47/30
[52] U.S. Cl. ....................................... 71/120; 71/121;
 71/DIG. 1; 71/86; 71/88; 71/90; 71/92; 71/93;
 71/94; 71/105; 71/106; 71/107; 71/108;
 71/109; 71/116; 71/117; 71/118
[58] Field of Search ..................... 71/120, 121, DIG. 1

[56] References Cited

U.S. PATENT DOCUMENTS

| | | | |
|---|---|---|---|
| 3,373,010 | 3/1968 | Olson | 71/121 |
| 4,295,877 | 10/1981 | Thizy et al. | 71/120 |
| 4,541,860 | 9/1985 | Civilla et al. | 71/DIG. 1 |
| 4,594,096 | 6/1986 | Albrecht et al. | 71/93 |

FOREIGN PATENT DOCUMENTS

| | | |
|---|---|---|
| 0022925 | 1/1981 | European Pat. Off. . |
| 0110174 | 6/1984 | European Pat. Off. . |
| 0142485 | 5/1985 | European Pat. Off. . |

*Primary Examiner*—Glennon H. Hollrah
*Assistant Examiner*—John D. Pak

[57] ABSTRACT

The invention relates to plant-protection agents which contain one or more active ingredients and which are based on suspoemulsions containing aqueous and organic phases, where the organic phase contains one or more surfactants from the group comprising the ethylene oxide/propylene oxide block polymers having an average molecular weight of 1,000–20,000. The suspoemulsions are subjected to large shear forces. Even thereafter, they exhibit a constant viscosity behavior, in spite of a large number of droplets and a low droplet size.

15 Claims, No Drawings

NOVEL SUSPOEMULSIONS OF ACTIVE INGREDIENTS FOR PLANT PROTECTION

This application is a continuation of application Ser. No. 096,909, filed Sept. 15, 1987, now abandoned.

In general, suspoemulsions are taken to mean formulations having at least three different phases, an aqueous, an organic and a solid phase. It is possible for water to function as an excipient phase in which one or more active ingredients are finely dispersed as the solid phase; the third phase in the suspoemulsion is then an organic solvent phase in which one or more active ingredients are present in emulsified form (EP-A 117,999 and EP-A 142,485). In principle, water-soluble active ingredients may also be dissolved in the aqueous phase.

The formulations described in EP-A 117,999 are storage-stable and applicationally ideal; however, under the action of large shear forces over a relatively long period of time, they may develop a very fine droplet distribution, which can lead to high viscosities of the finished formulation. In addition, there are certain active ingredient combinations of a relatively novel type which can be prepared by the process described therein only with limitations.

In EP-A 142,485, it is expressly pointed out that crystal formation can occur in the organic phase and that storage stability is only ensured for 1 month at elevated temperature. The object was therefore to develop novel suspoemulsions having improved applicational properties.

Surprisingly, it has now been found that suspoemulsions which contain one or, above all, several active ingredients and whose organic phase contains ethylene oxide/propylene oxide block polymers or ethoxylated polyarylphenol compounds as surfactants have advantageous properties. Although they contain very small droplets, they remain very highly flowable, do not tend towards crystal formation and are stable on storage. In addition, these suspoemulsions can also be applied in ULV (ultra low volume) form (Winnacker, Küchler: Chemische Technologie [Chemical Technology], vol. 7, Org. Techn. III, Carl Hanser Verlag Munich/Vienna (1986) pp. 322 ff.).

The invention therefore relates to plant-protection agents which are based on suspoemulsions containing aqueous and organic phases and which contain one or more active ingredients, wherein the organic phase contains one or more surfactants from the group comprising the ethylene oxide/propylene oxide block polymers having an average molecular weight of 1,000-20,000, such as, for example, HOE S 3510 (Hoechst AG), HOE S 1816 (Hoechst AG) and ®Rewopal PO (Rewo Chemie) or the ethoxylated polyarylphenol compounds or the mono- and/or polyalkylphenol compounds, such as, for example, the ®Arkopal or ®Sapogenat series from Hoechst AG, or mixtures thereof. Ethylene oxide/propylene oxide block polymers which can be used according to the invention are, in particular, the polymers of the formulae I and II below:

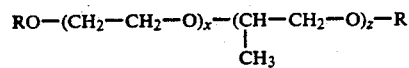 (I)

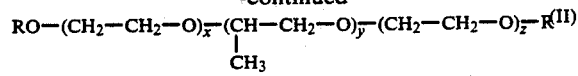 (II)

where, in these formulae, x, y and z, independently of one another, denote a number from 2 to 200 and R denotes H or ($C_1$-$C_{10}$)alkyl (HOE S 3510 (type I) and HOE S 1816 (type II)). Where R=H, the block polymers may also be phosphated, in particular monophosphated (HOE S 3618, type II). Possible ethoxylated polyarylphenol compounds are preferably tristyryl-substituted phenols containing 5-30 moles of EO[1]), such as, for example, HOE S 3474 (Hoechst AG) or ®Sopophor BSU (Rhône Poulenc).

[1]) EO=ethylene oxide

In general, the suspoemulsions contain two active ingredients.

Active ingredients employed in the organic phase are: 3,5-dihalo-4-hydroxybenzonitriles and esters and salts thereof, such as bromoxynil octanoat and ioxynil octanoat; substituted phenoxyacetic(propionic) acids and esters, such as mecoprop, 2,4-D ester and MCPA; (hetero)aryloxyphenoxy esters, such as fluazifop, fenoxaprop-ethyl and diclofop-methyl; phosphates, such as pyrazophos; fungicidal triazoles, such as propicanazole; pyrethroids, such as deltamethrin; aniline derivatives, such as pendimethalin, trifluralin, alachlor and metolachlor; imidazolecarboxamides, such as, for example, prochloraz; phenylurea derivatives, such as monolinuron; ethyl [3-(2-chloro-4-trifluoromethylphenoxy)-6-nitrobenzoyloxy]-acetate (RH 8301); N-[3-(1-ethyl-1-methylpropyl)-5-isoxazolyl]-2,6-dimethoxybenzamide (EL 107); [4-amino-3,5-dichloro-6-fluoro-2-pyridinyl]oxyacetic acid esters, in particular the isooctyl ester (fluroxypyr), or phenol derivatives, such as, for example, dinoseb or dinoseb acetate.

Suitable solvents for the organic phase are aromatic hydrocarbons, such as, for example, xylene, toluene and ½-methylnaphthalene; mixtures of ($C_6$-$C_{16}$)-aromatics, such as the ®Solvesso series with types 100, 150 and 200; water-immiscible ketones, such as, for example, isophorone, or substituted aromatics, such as, for example, halogenated aromatics. These solvents may also be admixed with ($C_1$-$C_{12}$)-phthalic acid esters as solubilizers; the latter may also completely replace the former.

Active ingredients which can be used for the aqueous phase are sulfur, carbendazim, triphenyltin hydroxide (TPTH), endosulfan, triazine derivaties, such as, for example, atrazine, simazine and cyanazine, dithiaanthraquinones, such as dithianon, dioxoimidazolidinecarboxamides, such as, for example, iprodione, pyridazinones, such as, for example, chloridazon, butenoates, such as binapacryl or phenylurea derivatives, such as, for example, linuron, isoproturon, diuron or chlortoluron, or mixtures thereof. These active ingredients are employed as ready formulations containing the conventional formulation auxiliaries, as described, for example, in EP-A 22,925, EP-A 110,174 and German Patent Application P 35 38 247.3.

The aqueous phase can contain the following dispersants: alkali metal salts of sulfosuccinic acid monoesters (prepared by reacting a polyglycol ether of a product of the condensation of ($C_8$-$C_{12}$)-alkylphenol and formaldehyde with maleic anhydride and an alkali metal sulfite), alkali metal salts of a sulfo group-containing product of the condensation of a phenol and formaldehyde, alkali metal, ammonium or amine salts of partial esters of alkyl polyglycol ether phosphates, alkali metal salts of a lignin sulfonic acid mixed with equal parts of a swellable alkaline-earth metal silicate, salts of polymerized alkylnaphthalenesulfonic acids or salts of ethoxylated alkylphenol novolaks. Furthermore, further conventional formulation auxiliaries, such as wetting agents, for example Na oleoyl N-methyltauride and tridecyl alcohol polyglycol ether, antifoaming agents based on tributyl phosphate or on silicone, antifreeze agents, such as, for example, ethylene glycol, propylene glycol and glycerol, alumosilicates having a leaf structure, such as montmorillonites or bentonites, safeners, such as, for example, urea, and conventional preservatives, such as benzoic acid and sorbitan acid, inter alia, may be added in addition.

The suspoemulsions according to the invention may contain, for example, the following active ingredient combinations: diclofop-methyl/isoproturon, deltamethrin/endosulfan, pyrazophos/sulfur, pendimethalin/chlortoluron, pyrazophos/carbendazim and/or TPTH, prochloraz/carbendazim, trifluralin/triazines (atrazine and simazine) and pyrazophos/dithianon.

The aqueous phase contains 0.1 to 70% by weight of active ingredient, 0.5 to 15% by weight of dispersant, 0.1 to 15% by weight of wetting agent, 0.1 to 5% by weight of antifoaming agent, 1.0 to 15% by weight of antifreeze and 0.01 to 4% by weight of alumosilicates.

In the organic phase, which contains the solvents cited above individually or in mixtures, the active ingredients are present in dissolved form. 0.1 to 90% by weight of active ingredient, 0.1 to 35% by weight of surfactant, but specifically 1.0 to 10.0% by weight, and 2 to 90% by weight of solvent are included.

The aqueous phase to organic phase ratio can vary within broad limits between 100:1 and 1:100, depending on the conditions.

In the case of application as aqueous suspension concentrates, the aqueous, dispersed phase to organic phase ratio is generally between 1:1 and 100:1, but preferably 1:1 to 20:1. In the case of a ULV application, the aqueous phase to organic phase ratio is 1:1 to 1:100, but preferably 2:3 to 1:20. In this case, the organic phase (oil) is then an excipient phase in which the aqueous phase, which contains the active ingredient(s) suspended there in solid form, is present as finely divided droplets.

The aqueous dispersion formulations are prepared in the known fashion by wet-grinding by means of bead, bore, sand or colloid or corundum-disk mills.

The active ingredients and surfactants of the organic phase are dissolved in the solvent with stirring and, if necessary, warming and subsequent cooling.

The aqueous, disperse phase and the organic phase containing the surfactant(s) and active ingredient(s) are subjected, in a known fashion (for example according to EP-A 117,999), to large shear forces, i.e. shear forces from $1$–$7,000$ sec$^{-1}$, during which the storage-stable suspoemulsions desired are obtained.

The invention is illustrated by the following examples.

TABLE 1

| Formulation examples (component data in % by weight) | | | | | | | | | | | | | |
| --- | --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 | 13 |
| Isoproturon Disp. | 40 | 40 | 40 | 67 | 75 | 54 | 37 | 91 | 91 | 72.5 | 40 | 48.5 |  |
| Linuron Disp. |  |  |  |  |  |  |  |  |  |  |  |  | 31.5 |
| Trifluralin | 18 | 18 | 18 |  |  |  | 16 |  |  |  | 18 |  |  |
| Fluroxypyr |  |  |  |  | 7.2 | 4 |  |  |  | 4.6 |  |  |  |
| EL 107 |  |  |  |  |  |  |  |  |  |  |  | 1.5 |  |
| RH 8301 |  |  |  |  |  |  |  | 1.4 |  |  |  |  |  |
| Pendimethalin |  |  |  | 9 |  |  | 7.5 |  |  |  |  |  |  |
| Alachlor |  |  |  |  |  |  |  |  |  |  |  |  | 31.2 |
| Bromoxynil octanoat |  |  |  |  |  | 4.6 |  |  |  |  |  |  |  |
| Ioxynil octanoat |  |  |  |  |  | 4.2 |  |  |  |  |  |  |  |
| Dinoseb (acetate) |  |  |  |  |  |  |  |  |  |  |  | 38.5 |  |
| Dioctyl phthalate |  | 28 |  | 20 |  |  |  |  |  | 3.3 | 10 | 25 |  |
| $^R$Solvesso 100 |  |  |  |  | 14.3 |  |  |  |  |  | 5 |  | 10.5 |
| $^R$Solvesso 150 | 28 |  | 28 |  |  | 15 | 26.7 | 6.6 | 3.3 |  | 5 |  |  |
| Xylene |  |  |  |  |  |  |  |  |  |  |  |  | 24.2 |
| Hoe S 3510 |  | 4 | 4 | 4 |  |  |  |  |  |  |  | 2.5 | 4 |
| Hoe S 1816 |  |  |  |  | 2.5 | 1 |  | 1 |  | 1 |  | 2.5 |  |
| HOE S 1816-1 | 2.5 |  |  |  |  |  |  |  |  |  |  |  |  |
| Hoe S 3474 |  |  |  |  |  |  |  | 2.5 |  |  |  |  |  |
| $^R$Soprophor BUSO |  |  |  |  |  |  |  |  | 1 |  |  |  |  |
| Water to 100 |  |  |  |  |  |  |  |  |  |  |  |  |  |
|  | 14 | 15 | 16 | 17 | 18 | 19 | 20 | 21 | 22 | 23 | 24 | 25 |  |
| Linuron Disp. | 31.5 | 31.5 | 31.5 | 31.5 | 39.5 |  |  |  |  |  |  |  |  |
| Sulfur Disp. |  |  |  |  |  | 70 | 70 | 80 |  |  |  |  |  |
| Carbendazim Disp. |  |  |  |  |  |  |  |  | 33 |  |  |  |  |
| Endosulfan Disp. |  |  |  |  |  |  |  |  |  | 30 |  |  |  |
| TPTH Disp. |  |  |  |  |  |  |  |  |  |  | 40 | 50 |  |
| Pyrazophos |  |  |  |  |  | 4 | 4 |  | 15 |  | 10 |  |  |
| Deltamethrin |  |  |  |  |  |  |  | 2 |  | 3 |  | 4 |  |
| Monolinuron |  |  |  |  | 15.6 |  |  |  |  |  |  |  |  |
| Alachlor | 31.2 | 31.2 | 31.2 |  |  |  |  |  |  |  |  |  |  |
| Metolachlor |  |  |  | 31.2 |  |  |  |  |  |  |  |  |  |
| Dioctyl phthalate |  |  |  |  |  | 12 | 12 |  | 12 |  |  |  |  |
| ¦ Methylnaphthalene |  |  |  |  |  |  |  |  | 30 |  | 22 | 12 |  |
| Xylene | 24.2 | 24.2 | 24.2 | 24.2 | 5 |  | 4 |  |  |  |  |  |  |
| Isophorone |  |  |  |  | 26.4 |  |  |  |  |  |  |  |  |
| Hoe S 3510 |  |  |  |  | 5.7 | 2 |  |  | 5 |  | 4.5 | 3.7 |  |
| Hoe S 1816 | 4 |  |  |  |  |  |  |  |  |  |  |  |  |
| HOE S 1816-1 |  | 4 |  |  |  |  |  |  |  | 4 |  |  |  |
| Hoe S 3474 |  |  | 4 |  |  | 2 |  |  |  |  |  |  |  |
| $^R$Soprophor BSU |  |  |  | 4 |  |  | 2 |  |  |  |  |  |  |

TABLE 1-continued

Formulation examples (component data in % by weight)

Water to 100

| | 26 | 27 | 28 | 29 | 30 | 31 | 32 | 33 | 34 | 35 | 36 | 37 | 38 |
|---|---|---|---|---|---|---|---|---|---|---|---|---|---|
| Isoproturon Disp. | 30 | | | | | | | | | | | | |
| Linuron Disp. | | 31.6 | 30 | 30.5 | 30.5 | | | | | | | | |
| Carbendazim Disp. | | | | | | 35 | 50 | 45 | 35 | 10 | | | |
| TPTH Disp. | | | | | | | | | | | 30 | 10 | |
| Dithianon Disp. | | | | | | | | | | | | | 30 |
| Pyrazophos | | | | | | | | | | 25 | | | |
| Prochloraz | | | | | | | | | | | 30 | | |
| Monolinuron | | | | | 5 | | | | | | | | |
| Alachlor | | 30 | | | | | | | | | | | |
| Metolachlor | | | | 30 | | | | | | | | | |
| Dioctyl phthalate | 60 | 27 | 60 | 27 | 50 | | | | | | 60 | | |
| ⅓ Methylnaphthalene | | | | | | | | | | | | | 63 |
| ᴿSolvesso 200 | | | | | | 63 | | | 35 | | | | |
| Xylene | | | | | | | 46 | 50 | | 55 | | 85 | |
| HOE S 3510 | 5 | 4 | 4 | 4 | 4 | | 4 | | 4 | | 4 | | 4 |
| Hoe S 1816 | | | | | | 2 | | 2 | | 2 | | | |
| HOE S 3618 | | | | | | | | | | | | 5 | |
| Water to 100 | | | | | | | | | | | | | |

| | 39 | 40 | 41 | 42 | 43 | 44 | 45 | 46 | 47 | 48 | 49 | 50 | 51 |
|---|---|---|---|---|---|---|---|---|---|---|---|---|---|
| Isoproturon Disp. | | | | 40 | 40 | 40 | 40 | 40 | 40 | | | | |
| Chlortoluron Disp. | | | | | | | | | | | | 30 | |
| Sulfur Disp. | | 30 | 30 | | | | | | | | | | |
| Endosulfan Disp. | | | | | | | | | | 30 | 30 | | |
| Atrazine Disp. | | | | | | | | | | | | | 30 |
| Dithianon | 30 | | | | | | | | | | | | |
| Pyrazophos | 14 | | 5 | | | | | | | | | | |
| Deltamethrin | | | | | | | | | | | 1 | | |
| Dichlofop-methyl | | | | | | | | | 10 | | | | |
| Trifluralin | | | | 18 | 18 | | 10 | 15 | | | | | |
| Pendimethalin | | | | | | 18 | | 8 | | | | | |
| Dioctyl phthalate | | 60 | 55 | | | | | | | 60 | 60 | 60 | 60 |
| ⅓ Methylnaphthalene | 50 | | | | | | | | | | | | |
| ᴿSolvesso 150 | | | | 33 | 33 | 33 | 33 | 35 | | | | | |
| Xylene | | | | | | | | | 45 | | | | |
| HOE S 3510 | | 5 | 5 | 2.5 | 5 | 2.5 | 5 | | | 5 | 5 | 5 | 5 |
| Hoe S 1816 | 2 | | | | | | | | 5 | | | | |
| Water to 100 | | | | | | | | | | | | | |

TABLE 2

(Comparison examples)
Isoproturon: Trifluralin = 200: 200 g/l

| | Viscosity [mPa.s] | | Droplet diameter [μm] | | | Recipe |
|---|---|---|---|---|---|---|
| | 112 [rpm] | 13 [rpm] | 50% | 75% | 90% | |
| I | 315 | 732 | 12.5 | 17.5 | 20.0 | According to |
| | 348 | 835 | 5.0 | 9.0 | 27.0 | Example 1 |
| | 343 | 860 | 3.4 | 8.0 | 16.0 | |
| | 287 | 570 | 2.2 | 4.0 | 7.0 | |
| | 311 | 680 | 2.0 | 3.5 | 8.5 | |
| II | 660 | 1702 | 5.3 | 6.6 | 7.6 | According to |
| | 648 | 1686 | 3.8 | 4.0 | 5.5 | Example 2 |
| | 660 | 1586 | 2.9 | 3.7 | 4.8 | |
| | 592 | 1442 | 2.65 | 2.95 | 3.6 | |
| | 653 | 1570 | 1.95 | 2.2 | 2.6 | |
| | 641 | 1678 | 1.55 | 1.95 | 3.0 | |
| III | 247 | 702 | 5.5 | 14.0 | 85.0 | According to |
| | 249 | 737 | 3.05 | 4.7 | 9.0 | Example 3 |
| | 239 | 665 | 2.5 | 3.7 | 7.8 | |
| | 233 | 634 | 2.0 | 2.6 | 3.6 | |
| IV | 434 | 1058 | 13.5 | 15.7 | 18.5 | According to |
| | 494 | 1152 | 2.95 | 3.6 | 4.4 | EP-A 117,999, |
| | 533 | 1326 | 1.85 | 2.05 | 2.2 | Example 1 |
| | 549 | 1431 | 1.35 | 1.65 | 1.85 | |
| | 621 | 1669 | <1 | 1.55 | 1.75 | |
| | 668 | 1814 | <1 | 1.35 | 1.65 | |

As shown by Table 2, the suspoemulsions according to the invention have a constant viscosity behavior, in spite of a large number of droplets and a small droplet size, in contrast to the known suspoemulsions according to EP-A 117,999.

We claim:

1. A herbicidal suspoemulsion composition with an aqueous and an organic phase, wherein the aqueous phase comprises 0.1 to 70% by weight of a herbicidally effective amount of active ingredient selected from the group consisting of linuron, isoproturon, diuron, chlortoluron and a mixture thereof, and the organic phase comprises 0.1 to 90% by weight of a herbicidally effective amount of active ingredient selected from the group consisting of trifluralin, pendimethalin and a mixture thereof, 0.1 to 35% by weight of one or more surfactants selected from the group consisting of ethylene oxide/propylene oxide block polymer of the formulae I and II

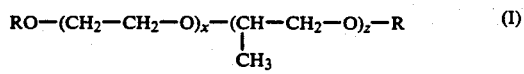

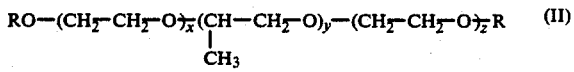

wherein X, Y and Z, independently of one another, denote a number from 2 to 200 and R denotes H or $(C_1-C_{10})$-alkyl, having an average molecular weight from 1,000 to 20,000 and 2 to 90% by weight of one or more organic solvents selected from the group consisting of aromatic hydrocarbons, mixture of $(C_6-C_{16})$-aromatics, water-immiscible ketones and halogenated aromatics.

2. A composition as claimed in claim 1, wherein the surfactant is a polymer of the formula II, wherein X and Z have the same meaning.

3. A composition as claimed in claim 1, wherein the organic phase comprises 1.0 to 10% by weight of surfactant.

4. A composition as claimed in claim 1, wherein the aqueous phase active ingredient is isoproturon and the organic phase active ingredient is trifluralin.

5. A composition as claimed in claim 1, wherein the one or more organic solvents are selected from the group consisting of xylene, toluene, 1- and 2-methylnaphthalene, mixture of ($C_6$–$C_{16}$)-aromatics and isophorone.

6. A composition as claimed in claim 1, wherein the organic solvent is a mixture of ($C_6$–$C_{16}$)-aromatics.

7. A composition as claimed in claim 1, wherein the surfactant is an ethylene oxide/propylene oxide block polymer of the formula I or II as defined in claim 1.

8. A composition as claimed in claim 7, wherein the aqueous phase active ingredient is isoproturon and the organic phase active ingredient is trifluralin.

9. A composition as claimed in claim 8, wherein the organic solvent is a mixture of ($C_6$–$C_{16}$)-aromatics.

10. A composition as claimed in claim 1, wherein the aqueous phase to organic phase ratio is between 100:1 to 1:100.

11. A composition as claimed in claim 1, wherein the composition is a suspension concentrate having an aqueous phase to organic phase ratio between 1:1 and 100:1.

12. A composition as claimed in claim 11, wherein the aqueous phase to organic phase ratio is 1:1 to 20:1.

13. A composition as claimed in claim 1, wherein the composition is a ULV-formulation having an aqueous phase to organic phase ratio of from 1:1 to 1:100.

14. A composition as claimed in claim 1, wherein the aqueous phase to organic phase ratio is 2:3 to 1:20.

15. A composition as claimed in claim 1, wherein the aqueous phase additionally comprises 0.1 to 15% by weight of dispersant or wetting agent or 1.0 to 5% by weight of antifoaming agent or 1.0 to 15% by weight of antifreeze or 0.01 to 4% by weight of alumosilicates or a mixture thereof.

* * * * *